United States Patent [19]

Miller

[11] 4,417,086

[45] Nov. 22, 1983

[54] EFFICIENT FLUIDIZED OLIGOMERIZATION

[75] Inventor: Stephen J. Miller, San Francisco, Calif.

[73] Assignee: Chevron Research Company, San Francisco, Calif.

[21] Appl. No.: 373,478

[22] Filed: Apr. 30, 1982

[51] Int. Cl.³ .............................................. C07C 2/02
[52] U.S. Cl. .................................. 585/530; 585/517; 585/533
[58] Field of Search ....................... 585/517, 530, 533

[56] References Cited

U.S. PATENT DOCUMENTS

| | | | |
|---|---|---|---|
| 2,678,904 | 5/1954 | Kearby et al. | 208/71 |
| 4,032,432 | 6/1977 | Owen et al. | 208/70 |
| 4,066,531 | 1/1978 | Owen et al. | 208/120 |
| 4,090,949 | 5/1978 | Owen et al. | 208/78 |
| 4,238,318 | 12/1980 | Kouwenhoven et al. | 585/409 |

Primary Examiner—Curtis R. Davis
Attorney, Agent, or Firm—D. A. Newell; S. R. La Paglia; W. L. Stumpf

[57] ABSTRACT

A highly efficient oligomerization process using molecular sieves is disclosed.

16 Claims, 2 Drawing Figures

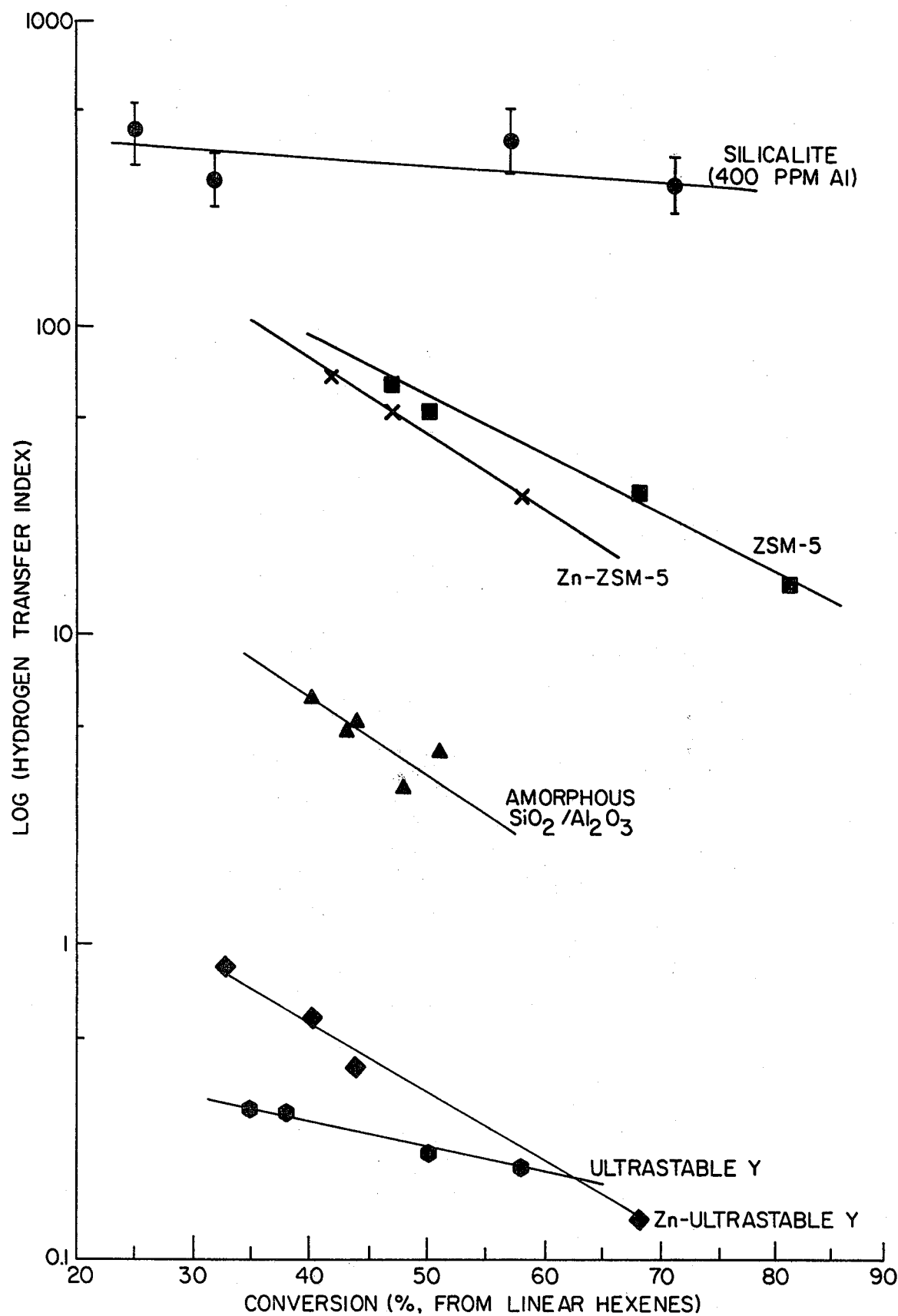
FIG.\_1.

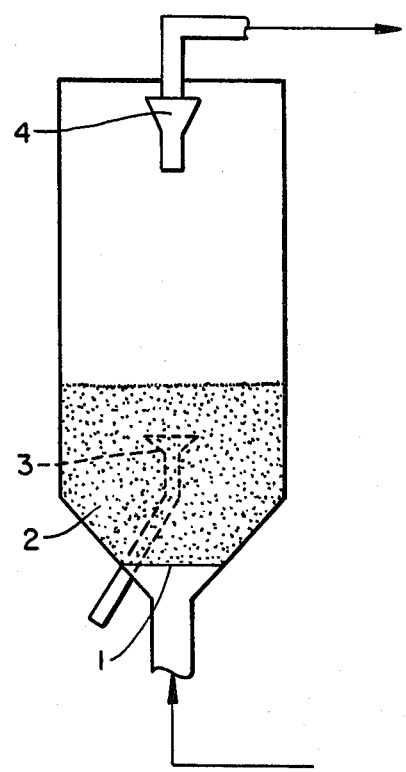
FIG._2.

3,417,086

EFFICIENT FLUIDIZED OLIGOMERIZATION

TECHNICAL BACKGROUND

One of the continuing problems in the refinery when using catalytic cracking processes is handling the very large amounts of gas produced. Catalytic cracking, and especially fluid catalytic cracking (FCC), is widely used in petroleum refineries in the United States. Refiners in the United States have more capacity for catalytic cracking than for any other single process except distillation. Those refiners have the capacity to catalytically crack over 6,100,000 barrels of oil per day (*Oil and Gas Journal,* Mar. 24, 1980). Since catalytic cracking is a nonhydrogenative process, it can be appreciated that huge amounts of olefinic gases are produced. Whenever the severity of a catalytic cracker is increased or the throughput is increased, even more olefinic gases are produced.

Recovering these enormous amounts of gas for further reaction requires large capital outlays for compressors and gas handling equipment. The alternative is to burn the olefinic gases as fuel for other parts of the refinery or as waste. Unfortunately, because the quantities of gas are huge and the capital costs are high, these gases are too often burned instead of recovered and reacted.

It can be appreciated that there is a highly intensive search for efficient, economical processes which would allow these reactive olefinic gases to be used further as chemicals rather than to be wasted but which do not require massive capital expenditures. This search for more efficient methods of using olefinic gases has continued for some time. U.S. Pat. No. 2,678,904, Kearby et al., May 18, 1954, for example, discloses polymerizing the olefins present in catalytic cracker effluent using a fluidized reaction bed containing an amorphous silica-alumina cracking catalyst. Other methods, using zeolites, have been proposed for processing heavier materials. U.S. Pat. No. 4,066,531, Owen et al., Jan. 3, 1978, discloses preparing the aromatics benzene, toluene, and the xylenes, from heavy reformates using zeolites and fluidized beds. U.S. Pat. No. 4,090,949, Owen et al., May 23, 1978, discloses upgrading poor quality olefinic gasolines by converting them in the presence of carbon/hydrogen contributing fragments using zeolites and fluidized beds. A recent disclosure relates to a combination process for catalytically cracking gas oils and upgrading the $C_6^-$ products using the same dual component zeolite catalyst in both steps. U.S. Pat. No. 4,032,432, Owen, June 28, 1977.

I have discovered that certain silicaceous crystalline molecular sieves can be used in a fluidized reaction zone to produce substantial amounts of olefin oligomers from the normally gaseous olefins produced by catalytic cracking. By oligomerizing all or part of the olefins, the volume of gas that needs to be handled is greatly decreased, plus, substantial amounts of more useful higher molecular weight olefin compounds are produced. Further, the fluidized oligomerization process can operate at the same pressure as the FCC reactor; the need for compressors is greatly lessened. This highly significant advantage occurs even if only part of the gas stream is fed to the oligomerization reactor. Importantly, because oligomerization is highly exothermic, the heat generated by the oligomerization reaction can be used to heat the feed to the oligomerization zone; the process is energy efficient by saving fuel as well as electricity necessary to operate compressors.

The catalysts used are highly stable and the reaction conditions are mild so that the catalyst charge to the oligomerization zone can have a very long service life. The necessity of burning coke deposits from the catalyst is greatly lowered. I have discovered that these surprising characteristics can be taken advantage of in an extremely efficient oligomerization process. The process of my invention has high conversions of gaseous olefins, is simple to operate, and has a small pressure drop, good mixing and a long run life.

TECHNICAL DISCLOSURE

My discoveries are embodied in a fluidized oligomerization process, comprising:

contacting a feed, which comprises olefins, with a fluidizable oligomerization catalyst, which comprises an intermediate pore size silicaceous crystalline molecular sieve, in a fluidized reaction zone containing said catalyst, wherein said zone comprises at least a first part into which said feed is introduced and at least a second part into which a stripping gas is introduced, and wherein said catalyst is circulated between said first part and said second part, such that at least part of said olefins are oligomerized in said first part and at least part of the olefin oligomers so produced are stripped from said catalyst in said second part.

I have discovered, that because the molecular sieves are surprisingly efficient oligomerization catalysts, they can be used very efficiently and effectively in a fluidized bed oligomerization reactor. In typical operation, the feed olefins are introduced into a fluidized bed reactor where they contact the oligomerization catalyst and are oligomerized. By the natural circulation in the reactor, the catalyst particles and adsorbed/absorbed oligomers pass upward into a stripping zone where the oligomers are stripped from the catalyst. The oligomers are then recovered from the overhead gas stream and the stripped catalyst circulates downward to come in contact with more feed and to oligomerize the olefins in it. The process is surprisingly efficient at least in part because the catalyst is freed and cleansed of coke precursors by the continuous stripping, yet catalytic efficiency is maintained. Further, because separate regeneration reaction zones are not needed, since the catalyst is effectively rejuvenated in situ, the problems associated with such separate regeneration zones are avoided. Ex situ regeneration of all or part of the catalyst charge can be carried out as practiced in the art if desired. A separate regeneration zone is not needed, however, because the catalyst has a long service time in the present invention. High gas flow rates to transfer catalysts from reaction zone to regeneration zone are unnecessary. Pipe erosion by the particles between reactor and regenerator is eliminated. And most importantly, the attrition rate of the catalyst particles themselves is very greatly reduced; less catalyst is needed, fewer fines are produced and operation is made easy and commercially very attractive.

Although in standard operation the fluidized reaction zone will have just one oligomerization part and one subsequent stripping part, both feed and stripping gas can be introduced in stacked operation; multiple feed and stripping gas inlets can be used. If multiple inlets are used, however, it is preferred that each oligomerization section be followed by a stripping gas section.

The feed is typically introduced into the bottom of the reaction zone and passed into contact with the catalyst through porous grids or other dispersal means which retain the catalyst and promote an even gas flow rate through the reaction zone. The stripping gas can be introduced by any convenient method which will cause the gas to come in contact with the catalyst particles as they circulate from the bottom to the top of the bed. It is preferred that the means by which the stripping gas is introduced passes through the oligomerization part of the reaction zone so that the stripping gas temperature is maintained. Although steam is the preferred stripping gas, other standard stripping gases can be used. Normally, there will be a separator to ensure that the gaseous product and any catalyst particles which might be carried to the outlet of the reactor are separated. The process of my invention is especially useful in the processes disclosed in my copending patent application Ser. No. 373,479, filed Apr. 30, 1982, and incorporated by reference.

The feed olefins can be prepared from any source by standard methods. The feed need only contain gaseous olefins, as opposed to liquid olefins, so the catalyst bed can be fluidized. Sources of lower olefins can include FCC offgas, syngas (by use of CO reduction catalysts), low pressure, nonhydrogenative zeolite dewaxing, alkanols (by using high silica zeolites), dewaxing with crystalline silica polymorphs, and thermal cracking offgas. The olefins can contain up to 6 or 7 carbon atoms but are preferably propene, $C_4$ olefins, and their mixtures. The preferred feed sources are FCC offgas, nonhydrogenative zeolite dewaxing offgas, and offgas from dewaxing with crystalline silica polymorphs.

The preferred olefins, if process streams are not used, are straight chain, or n-olefins, and the preferred n-olefins are 1-olefins.

By "intermediate pore size silicaceous crystalline molecular sieve," as used herein, is meant two classes of silica-containing crystalline materials. The first class includes materials which, in addition to silica, contain significant amounts of alumina. These crystalline materials are usually called "zeolites", i.e., crystalline aluminosilicates. The second class of materials are essentially aluminum-free silicates. These crystalline materials can include crystalline silica polymorphs, e.g., silicalite; chromia silicates, e.g., CZM; and ferrosilicates, e.g., U.S. Pat. No. 4,238,318.

All of these materials have the ability of sorting molecules based on the size or the shape, or both of the molecules. The larger pore size materials will admit larger molecules than the smaller pore size materials. Intermediate pore size silicaceous crystalline molecular sieves have the unique characteristics of being able to differentiate between large molecules and molecules containing quaternary carbon atoms on the one hand, and smaller molecules on the other. Thus, the intermediate pore size materials have surprising catalytic selectivities by reason of their effective pore apertures, as well as highly desirable and surprising activity and stability when compared to larger pore size crystalline molecular sieves.

By "intermediate pore size," as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size, or kinetic pore size, of the molecular sieves can be measured using standard adsorption techniques, and hydrocarbonaceous compounds of known minimum kinetic diameters. See Breck, *Zeolite Molecular Sieves*, 1974 (especially Chapter 8) and Anderson et al., J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene) (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. Among the materials falling within this range are the zeolite ZSM-5, the crystalline silica polymorph silicalite, U.S. Pat. No. Re. 29,948 organosilicates, and the chromia silicate, CZM.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

Examples of intermediate pore size silicaceous crystalline molecular sieves include zeolites such as ZSM-5, ZSM-11, ZSM-12, ZSM-21, ZSM-23, ZSM-35, and ZSM-38. ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 and ZSM-38 are described in U.S. Pat. No. 3,948,758; ZSM-23 is described in U.S. Pat. No. 4,076,842; ZSM-35 is described in U.S. Pat. No. 4,016,245. These patents and specifications are incorporated herein by reference. The intermediate pore size materials can include "crystalline admixtures" which are thought to be the result of faults occurring within the crystal or crystallite area during the synthesis of the zeolites. The "crystalline admixtures" are themselves zeolites but have characteristics in common, in a uniform or nonuniform manner, to what the literature reports as distinct zeolites. Examples of crystalline admixtures of ZSM-5 and ZSM-11 are disclosed and claimed in U.S. Pat. No. 4,229, 424, Kokotailo, Oct. 21, 1980 (incorporated by reference). The crystalline admixtures are themselves intermediate pore size zeolites and are not to be confused with physical admixtures of zeolites in which distinct crystals or crystallites of different zeolites are physically present in the same catalyst composite or hydrothermal reaction mixture.

Other examples of intermediate pore size silicaceous crystalline molecular sieves include crystalline silica polymorphs which, as described before, are essentially aluminum-free.

"Essentially aluminum-free," as used herein, is meant the product silica polymorph (or essentially aluminum-free silicaceous crystalline molecular sieve) has a silica:alumina mole ratio of greater than 200:1, preferably greater than 500:1, and more preferably greater than 1000:1. The term "essentially aluminum-free" is used because it is difficult to prepare completely aluminum-free reaction mixtures for synthesizing these materials. Especially when commercial silica sources are used, aluminum is almost always present to a greater or lesser degree. The hydrothermal reaction mixtures from which the essentially alumina-free crystalline silicaceous molecular sieves are prepared can also be referred to as being substantially aluminum-free. By this usage is meant that no aluminum is intentionally added to the reaction mixture, e.g., as an alumina or aluminate reagent, and that to the extent aluminum is present, it occurs only as a contaminant in the reagents.

Essentially alumina-free intermediate pore size crystalline silicas include silicalite, disclosed in U.S. Pat. No. 4,061,724; and "U.S. Pat. No. Re. 29,948 organosilicates" as disclosed in U.S. Pat. No. Re. 29,948. Intermediate pore size silicas, ferrosilicates and galliosilicates are disclosed in U.S. Pat. No. 4,238,318, Kouwenhoven et al., Dec. 9, 1980. Intermediate pore size chromia silicates, CZM, are disclosed in Ser. No. 160,618, Miller, filed June 28, 1980. All of these are incorporated by reference.

The most preferred molecular sieves are the zeolites ZSM-5, ZSM-11, and their crystalline admixtures, silicalite, U.S. Pat. No. Re. 29,948 organosilicates, and CZM. Of course, these and other molecular sieves can be used in physical admixtures.

Zeolitic silicaceous crystalline molecular sieve catalysts can be made surprisingly more active and stable for oligomerization by including Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (such as nickel, cobalt, palladium, and platinum) as well as other metals (such as chromium, vanadium, titanium, manganese, and rhenium) may be included in the catalyst. Mixtures of these metals may also be present. Strongly basic metals such as the alkali metals are unsatisfactory as they poison substantially all of the polymerization sites on the zeolite. For this reason, the alkali metal content of the zeolite, or other molecular sieve, is less than 1%, preferably less than 0.1%, and most preferably less than 0.01%. The most preferred substituents for use are zinc and zinc compounds. The amount of zinc used is typically from about 0.01 to about 10 wt. % based on the metal.

The molecular sieves can be composited with inorganic matrix materials, or they can be used with an organic binder. Standard methods for incorporating zeolites into FCC catalysts and for preparing fluidizable catalysts can be used to prepare the fluidizable oligomerization catalysts. It is preferred to incorporate the molecular sieve into an inorganic matrix since the molecular sieves, because of their large internal pore volumes, tend to be fragile, and to be subject to physical collapse and attrition during normal operation of the fluid reaction zone. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be cracked or converted to paraffins and aromatics which are not as chemically reactive as the olefin oligomers. It is highly preferred to use the attrition-resistant particles disclosed in my copending patent application Ser. No. 375,439, filed May 6, 1982, and incorporated by reference.

Where the molecular sieves are composited with binder materials, polymerization processes of the present invention are surprisingly more efficient with small crystallite sieve particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The reaction conditions under which the oligomerization reactions take place include a pressure of subatmospheric to several hundred atmospheres, but is preferably 10 bar or less, and most preferably 0 to 6 bar.

The reaction zone is operated below about 400° C., since above that temperature not only significant cracking of reactants and loss of oligomer product take place, but also significant hydrogen transfer reaction causing loss of olefinic oligomers to paraffins and aromatics takes place. The reaction zone temperatures are preferably from about 150° C. to 350° C. Gas hourly space velocities sufficient to fluidize the catalyst bed are used. Gas hourly space velocities typically range from about 1000 to 3000.

Once the effluent from the oligomerization reaction zone is recovered, a number of further processing steps can be performed. The effluent of the fluidized polymerization process will contain substantial amounts of olefins of longer chain length (higher boiling point) than the feed olefins. Depending upon the molecular sieve being used, these higher boiling olefins may crack and reassemble to form a continuum of higher molecular weight compounds rather than a pure oligomeric product.

By "conversion" as used herein is meant that certain amounts of feed olefins will be converted to higher molecular weight, higher boiling olefinic products. At least 30% of the feed olefins are converted to higher boiling olefins, preferably more than 50%, and most preferably more than 70% by weight.

If it is desired to use the longer chain compounds which have been formed as mid-distillates, the olefinic product can be hydrogenated.

All or part of the effluent can be contacted with the molecular sieve catalyst in further reaction zones to react unreacted olefins and olefin oligomers with themselves and each other to form still longer chain materials. Of course, the longer the carbon chain, the more susceptible the compound is to being cracked. Therefore, where successive oligomerization zones are used, each is limited to reaction conditions less severe than the preceding oligomerization zones. Operating with oligomerization zones in series with decreasing severity can also make process control of the exothermic oligomerization reactions much easier.

One particularly desirable method of operation is to separate unreacted olefins present in the effluent of the fluid reaction zone from the olefin oligomers present in the effluent and then to recycle the unreacted alkenes back into the fluidized zone.

The run life of the catalyst in the oligomerization reaction zone can be further increased by periodically stopping the flow of feed into the reaction zone and stripping the catalyst with a stripping gas (such as hydrogen, nitrogen, water vapor).

A highly energy efficient method of operating the present process is to contact the feed with the reaction zone effluent through a heat exchanger. By this means, the heat generated by the highly exothermic oligomerization reactions can be used to heat the feed and substitute for furnace capacity.

FIGURES

FIG. 1 illustrates data having differences between the hydrogen transfer indices of several catalysts as well as the response of the hydrogen transfer indices to fouling.

FIG. 2 illustrates a reaction vessel in which the present process would be practiced. The olefinic feed is introduced through a porous grid (1) or other vapor distributor located near the bottom of the reactor and rises through a bed of fluidized catalyst (2) located within the reactor. The stripping gas is introduced by means of pipe and a second porous grid (3) or other vapor distributor located above the feed inlet but below the top of the fluidized catalyst. The product oligomer stream is recovered from the top of the reactor after passing through a separator (4).

The Examples illustrate the invention without limiting it.

EXAMPLE 1

A series of experiments was performed to examine the hydrogen transfer activity of molecular sieves. A feed pulse of fixed volume (0.5 microliter) from a heated Valco valve was carried into a small, fixed catalyst bed located in a stainless steel reactor. The reaction was entirely gas phase and isothermal. The hydrocarbon feed pulse was carried to the catalyst bed by a known velocity nitrogen stream at a high linear rate. The nitrogen stream was passed through a 4A/5A molecular sieve purifier before contacting the feed. The catalyst bed contained $-250$ mesh catalyst fines which, depending on the catalyst, were diluted with the same size mesh alumina. The diluent alumina was added as needed to reduce the catalyst activity so all catalysts could be measured at roughly identical feed conversions. The catalyst was finally diluted (4:1) with 80–100 mesh, acid washed Alundum to improve catalyst dispersion and to help maintain a true isothermal bed temperature. Reactor pressure was controlled by an Annin valve.

The entire gas stream, containing the reacted feed pulse, was taken directly through heated lines to the injector splitter of a capillary gas chromatograph equipped with a flame ionization detector.

The reaction conditions include a catalyst temperature of 221° C. (430° F.), total pressure of 34.5 bar (500 psi) and a nitrogen carrier gas flow of 800 cc/min. at STP. The injection volume was 0.5 microliter. Hydrocarbon analysis was performed using a 50-meter OV-101 fused silica capillary column. The catalyst was continually exposed to the nitrogen carrier gas between injections.

The hydrogen transfer index calculated from the test results in the ratio of 3-methylpentenes to 3-methylpentane produced from a 1-hexene feed, with a linear hexene conversion from 30% to 70%.

The contact time was computed from the temperatures and pressure corrected linear velocity of the nitrogen carrier stream and the length and volume of the catalyst bed. The computed WHSV and catalyst/oil ratio were based solely on the active component content within the bed.

The catalysts tested are listed in Table 1.

TABLE 1

| Catalyst | $SiO_2/Al_2O_3$ Mole Ratio |
|---|---|
| (A) ZSM-5 | 78:1 |
| (B) Silicalite | 230:1 |
| (C) Silicalite | 2200:1 |
| (D) Ultrastable Y | 6:1 |
| (E) Dealuminated Mordenite | 63:1 |
| (F) Amorphous $SiO_2/Al_2O_3$ | 54/46 (wt. ratio) |
| (G) ZSM-12 | 50:1 |

The results obtained are listed in Table 2. Experiments with Catalysts (A) and (B) were performed after impregnating the catalysts with 0.8 wt. % zinc.

TABLE 2

| Catalyst | 20% A 80% $Al_2O_3$ | 20% A 80% $Al_2O_3$ | 65% B | 65% C | 12% D 88% $Al_2O_3$ | 18% E 82% $Al_2O_3$ | 100% F | 100% G |
|---|---|---|---|---|---|---|---|---|
| Inj. Number | 3 | 3 | 3 | 2 | 3 | 1 | 2 | 1 |
| Catalyst Wt. (mg Sieve) | 4.4 | 4.1 | 19 | 24 | 2.8 | 4.2 | 35 | 19.3 |
| Zn (0.8%): Yes/No | No | Yes | Yes | No | No | No | No | No |
| Alundum Dilution | 4:1 | 4:1 | 4:1 | 3:1 | 4:1 | 4:1 | 4:1 | 4:1 |
| Contact Time (sec) | 0.25 | 0.36 | 0.33 | 0.41 | 0.28 | 0.23 | 0.34 | 0.4 |
| WHSV (1/hr) | 1100 | 806 | 200 | 120 | 1500 | 1220 | 100 | 157 |
| Cat/Oil | 13 | 12 | 57 | 71 | 9 | 13 | 104 | 57 |
| Conversion From Linear Hexenes (%) | 47 | 42 | 41 | 56 | 38 | 48 | 43 | 53 |
| $K_{Hexenes}$ (1/sec) | 2.54 | 1.51 | 1.60 | 2.00 | 1.71 | 2.84 | 1.65 | 1.88 |
| Product Yield, Wt. % | | | | | | | | |
| $C_4$ Minus | 13 | 12.6 | 14 | 13.3 | 3.5 | 17.1 | 0.3 | 12 |
| $C_5$ | 11 | 10 | 8.4 | 8.5 | 4.2 | 12.9 | 3 | 8 |
| $C_6$ | 57 | 58.8 | 62 | 53.6 | 63.2 | 55.7 | 76.4 | 73 |
| $C_7$ | 4 | 4.2 | 4.1 | 5.5 | 4.7 | 4.4 | 3.5 | 2 |
| $C_8$ | 7.5 | 5.6 | 5.4 | 7.9 | 5.9 | 5.2 | 4.1 | 3.7 |
| $C_9$ | 4 | 3.6 | 2.5 | 4.3 | 4.3 | 2.4 | 2.4 | 1.3 |
| $C_{10}{}^+$ | 1.9 | 2.8 | 2.3 | 4.9 | 10.7 | 1.1 | 10.1 | 0.3 |

TABLE 2-continued

| Catalyst | 20% A 80% Al$_2$O$_3$ | 20% A 80% Al$_2$O$_3$ | 65% B | 65% C | 12% D 88% Al$_2$O$_3$ | 18% E 82% Al$_2$O$_3$ | 100% F | 100% G |
| --- | --- | --- | --- | --- | --- | --- | --- | --- |
|  | Hydrogen Transfer Index | | | | | | | |
| 3M-Pentenes/ 3M-Pentane | 66 | 70 | 105 | 500 | 0.30 | 1.0 | 5 | 6 |

The graph of FIG. 1 illustrates the differences in hydrogen transfer index for several catalysts, as well as the response of the hydrogen transfer index to the number of hexene injections, i.e., to the fouling of the catalyst. The higher the hydrogen transfer index, the lower the hydrogen transfer activity of the catalyst. The hydrogen transfer index should be above 10, preferably above 25.

EXAMPLE 2

A ZSM-5 catalyst was made as follows.

720 g of Claylok Alumina (23% Al$_2$O$_3$ by weight), 1440 g concentrated HNO$_3$ and 540 g H$_2$O were mixed together. Then 3960 g Ludox AS (30% SiO$_2$ by weight) were added and the mixture heated to 100° F. (38° C.) and stirred for 30 minutes.

To the mixture was then added a solution of 1512 g concentrated NH$_4$OH plus 3960 g H$_2$O. The mixture was then heated to 150° F. (66° C.) and stirred for 30 minutes.

Next, 360 g HZSM-5 (80 SiO$_2$/Al$_2$O$_3$, about 1 micron in diameter) were added at 150° F. (66° C.) with mixing. Mixing continued for 30 minutes. The mixture was put into a 5-gallon pail with a plastic liner.

The mixture was passed through a laboratory tower spray dryer using conventional methods to produce an FCC-type catalyst.

The catalyst was calcined in an oven with the temperature programmed at 100° F. (55.5° C.)/hour up to 850° F. (454° C.), held there for 8 hours, and then cooled. The catalyst was then exchanged five times for 1 hour each with a 25% ammonium acetate solution at 180° F. (82° C.), filtered, and dried overnight in a vacuum oven at 300° F. (149° C.). It was finally calcined for 8 hours at 850° F. (454° C.).

The following catalyst inspections were obtained:

| Percent zeolite, by XRD | 17 |
| --- | --- |
| Average particle size, microns, by Microtrac analysis | 84 |
| Na, ppm | 180 |

30 cc of catalyst were placed in a fluidized bed reactor similar to that shown in FIG. 2 with about one-fourth of the fluidized catalyst bed above the steam exit. Fluidization was accomplished by feeding a 75% propylene-25 % propane mixture (80 liquid cc/hour) to the bottom of the reactor. The reactor was enclosed in a clamshell furnace which was used to maintain a bed temperature of 600° F. (316° C.) as indicated by an internal thermocouple. The rate of water (for steam-stripping the catalyst) to the unit was 12.5 cc/hour. The inlet hydrocarbon GHSV was calculated to be about 1500.

Product was collected between 7 and 10 hours onstream. The conversion to C$_4$+ during that time averaged 70 wt. %. Conversion to C$_5$+ was 61 wt. %.

What is claimed is:

1. A fluidized oligomerization process, comprising: contacting a feed, which comprises olefins, with a fluidizable oligomerization catalyst, which comprises an intermediate pore size silicaceous crystalline molecular sieve, in a fluidized reaction zone containing said catalyst, wherein said zone comprises at least a first part into which said feed is introduced and at least a second part into which a stripping gas is introduced, and wherein said catalyst is circulated between said first part and said second part, such that at least part of said olefins are oligomerized in said first part and at least part of the olefin oligomers so produced are stripped from said catalyst in said second part.

2. The process of claim 1 wherein said feed is the normally gaseous effluent of a catalytic cracking zone.

3. The process of claim 1 wherein said olefins comprise C$_3$ and C$_4$ olefins.

4. The process of claim 1 wherein said molecular sieve is a zeolite.

5. The process of claim 4 wherein said zeolite is ZSM-5, ZSM-11, crystalline admixtures thereof, or physical admixtures thereof.

6. The process of claim 1 wherein said molecular sieve is essentially aluminum-free and has a silica:alumina mole ratio of greater than 200:1.

7. The process of claim 6 wherein said molecular sieve is silicalite, a crystalline metal organosilicate disclosed in U.S. Pat. No. Re. 29,948, or CZM.

8. The process of claim 1 wherein said catalyst further comprises zinc or a compound thereof, cadmium or a compound thereof, or mixtures thereof.

9. The process of claim 5 or 7 wherein said catalyst further comprises zinc or a compound thereof.

10. The process of claim 7 wherein said molecular sieve comprises attrition-resistant particles.

11. The process of claim 1 wherein said stripping gas is steam.

12. The process of claim 1, further comprising: hydrogenating at least part of the effluent of said oligomerization reaction zone.

13. The process of claim 1, further comprising: introducing at least part of the olefin oligomers present in the effluent from said oligomerization reaction zone into at least one further oligomerization reaction zone.

14. The process of claim 13 wherein said olefin oligomers are contacted in said further oligomerization reaction zone with an intermediate pore size silicaceous molecular sieve under reaction conditions such that at least some of said oligomers are liquids.

15. The process of claim 1 wherein the temperature in said oligomerization reaction zone is less than about 400° C.

16. The process of claim 1, further comprising: separating unreacted olefins from the effluent of said reaction zone and recycling said unreacted olefins into said feed.

* * * * *

UNITED STATES PATENT AND TRADEMARK OFFICE
CERTIFICATE OF CORRECTION

PATENT NO. : 4,417,086
DATED : November 22, 1983
INVENTOR(S) : Stephen J. Miller It is certified that error appears in the above-identified patent and that said Letters Patent are hereby corrected as shown below:

Col. 1, line 50, "$C_6-$" should read --$C_6^-$--.

Col. 4, line 36, "Re. 29,948" should read --RE 29,948--.

Col. 4, line 64, "4,229, 424" should read --4,229,424--.

Col. 5, line 27, "Re. 29,948" should read --RE 29,948--.

Col. 5, line 28, "Re. 29,948" should read --RE 29,948--.

Col. 5, line 37, "Re. 29,948" should read --RE 29,948--.

Col. 10, line 37, "Re. 29,948" should read --RE 29,948--.

Signed and Sealed this

Nineteenth Day of June 1984

[SEAL]

Attest:

GERALD J. MOSSINGHOFF

Attesting Officer   Commissioner of Patents and Trademarks